United States Patent
Vertenoeuil et al.

(10) Patent No.: US 9,746,394 B2
(45) Date of Patent: Aug. 29, 2017

(54) BENCH TEST, FOR THE CHARACTERIZATION OF A FLOW OF A TWO-PHASE FLUID

(71) Applicant: SNECMA, Paris (FR)

(72) Inventors: Philippe Vertenoeuil, Paris (FR); Petar Tomov, Montreuil (FR)

(73) Assignee: SNECMA, Paris (FR)

( * ) Notice: Subject to any disclaimer, the term of this patent is extended or adjusted under 35 U.S.C. 154(b) by 235 days.

(21) Appl. No.: 14/676,211

(22) Filed: Apr. 1, 2015

(65) Prior Publication Data
US 2015/0276554 A1    Oct. 1, 2015

(30) Foreign Application Priority Data

Apr. 1, 2014    (FR) ..................................... 14 52890

(51) Int. Cl.
| | |
|---|---|
| G01M 15/14 | (2006.01) |
| G01N 33/28 | (2006.01) |
| G01F 1/44 | (2006.01) |
| G01F 1/74 | (2006.01) |

(52) U.S. Cl.
CPC ............... *G01M 15/14* (2013.01); *G01F 1/44* (2013.01); *G01F 1/74* (2013.01); *G01N 33/28* (2013.01)

(58) Field of Classification Search
CPC . G01F 1/44; G01F 1/74; G01M 15/14; G01N 33/28; G01N 25/52; G01N 27/223
See application file for complete search history.

(56) References Cited

U.S. PATENT DOCUMENTS

| | | | | |
|---|---|---|---|---|
| 2,976,720 | A * | 3/1961 | Callahan | G01N 27/223 73/61.43 |
| 4,656,827 | A * | 4/1987 | Puillet | F02C 7/22 137/599.05 |
| 6,260,426 | B1 * | 7/2001 | Wharton | G01N 33/28 73/865.9 |
| 9,354,141 | B1 * | 5/2016 | McElrath | G01M 15/14 |
| 9,395,274 | B2 * | 7/2016 | Dussap | B64D 47/00 |
| 2015/0184594 | A1 * | 7/2015 | Stammen | F02C 9/46 60/776 |

OTHER PUBLICATIONS

French Preliminary Search Report and Written Opinion issued Mar. 9, 2015, in Patent Application No. FR 1452890, filed Apr. 1, 2014 (with English Translation of Category of Cited Documents).
"Aircraft Engine Fuel Pump Cavitation Endurance Test", SAE The Engineering Society for Advancing Mobility Land Sea Air and Space, ARP492, Revision C, XP 008175304, Dec. 1994, 14 pages.
I. E. Dorofeeva, et al., "Cavitation of JP-8 Fuel in a Converging-Diverging Nozzle: Experiments and Modeling", Proceedings of the 7$^{th}$ International Symposium on Cavitation, CAV2009, Paper No. ##, XP 055174617, Aug. 2009, 10 pages.

* cited by examiner

*Primary Examiner* — Freddie Kirkland, III
(74) *Attorney, Agent, or Firm* — Oblon, McClelland, Maier & Neustadt, L.L.P.

(57) ABSTRACT

The invention provides a test bench for characterizing a flow of a two-phase fluid, the test bench comprising a fluid tank, a first pump suitable for taking fluid from the tank and for feeding first and second lines connected in parallel, each line being provided in succession, from upstream to downstream in the flow direction of the fluid, with: injection means for injecting air into the fluid; measurement means suitable for providing information about the proportion of the vapor phase relative to the liquid phase of the fluid; and a second pump or a Venturi.

11 Claims, 2 Drawing Sheets

BENCH TEST, FOR THE CHARACTERIZATION OF A FLOW OF A TWO-PHASE FLUID

BACKGROUND OF THE INVENTION

Field of the Invention

The present invention relates to a test bench for characterizing a flow of a two-phase fluid, in particular a flow of fuel for feeding to a turbine engine, such as an airplane turboprop or turbojet.

Description of the Related Art

Such a turbine engine is conventionally provided with a fuel pump having a low pressure stage, referred to as the low pressure pump, and a high pressure stage, referred to as the high pressure pump. The low pressure pump is for generating a pressure rise, and it is generally formed by a centrifugal pump having a bladed impeller. Its pressure raising characteristics depend strongly on the speed of rotation of the pump. The high pressure pump is for generating a flow rate. These two pumps are usually incorporated in a common housing and they are driven at the same speed by a shaft.

Physical phenomena modify significantly the characteristics with which the turbine engine is fed in operation, these phenomena depending in particular on the shape of the fuel feed pipe, on altitude, and on the type of fuel used. In particular, in operation, air dissolved in the fuel (kerosene) tends to gas out and the kerosene can vaporize. The fluid flowing in the pipe and through the fuel pump is thus a two-phase fluid containing bubbles or pockets of gas that can lead to malfunctions of the turbine engine (fluctuations in thrust, loss of control, engine stopping, etc.).

For safety reasons, it is necessary to be able to guarantee that turbine engines can tolerate this type of phenomenon, regardless of operating conditions. Nevertheless, these phenomena are poorly known at present and it is relatively difficult to model them or to reproduce them during testing. It therefore appears to be necessary to be able to study and to characterize such phenomena. In particular, such characterization involves having knowledge of the ratio representing the proportion of the vapor phase relative to the liquid phase of the fuel.

At present, the only standard dealing with the quantity of gas and the gas factor in an airplane fuel feed system is the ARP 492 standard. That standard is relatively old and does not enable the above-mentioned phenomena to be studied reliably.

For safety reasons, present-day pumps are overdimensioned so as to guarantee proper operation of the turbine engine under all operating conditions. Nevertheless, such overdimensioning is unfavorable in terms of weight and size, in particular.

BRIEF SUMMARY OF THE INVENTION

An object of the invention is to provide a solution to the above-mentioned problems that is simple, effective, and inexpensive.

To this end, the invention provides a test bench for characterizing a flow of a two-phase fluid, the bench comprising a fluid tank, a first pump suitable for taking fluid from the tank and for feeding first and second lines that are connected in parallel;

the first line being provided in succession, from upstream to downstream in the fluid flow direction, with: first means for injecting air into the fluid; first measurement means suitable for providing information about the proportion of vapor phase relative to the liquid phase of the fluid; and a second pump suitable for simulating a turbine engine fuel pump, in particular a low pressure pump of a turbine engine;

the second line being provided in succession, from upstream to downstream in the flow direction of the fluid, with: second means for injecting air into the liquid, second measurement means suitable for providing information about the proportion of the vapor phase relative to the liquid phase of the fluid; and a suction-generator member, e.g. a Venturi.

It should be recalled that a suction-generator member serves to limit the flow of a fluid by creating differential pressure across the member.

It should also be recalled that a Venturi is a member having a progressively converging zone followed by a progressively diverging zone.

The test bench of the invention thus proposes two parallel lines, so as to study the effect of the second pump (low pressure or LP pump) by comparing the ratio V/L (where V is the proportion of the vapor phase in the fluid and L is the proportion of the liquid phase) between the first line including the second pump and the second line including the suction-generator member, of characteristics that are well known and easy to model. It is thus possible to separate the influence of the low pressure or LP pump (as simulated by the second pump) from the influence of the remainder of the fuel feed system.

In particular, it is possible to vary the speed of rotation of each of the first and second pumps, and also to vary the flow rate of air injected by the corresponding means.

Studying the V/L ratios can serve in particular to validate or refine mathematical models so that they represent as accurately as possible the phenomena that take place during the operation of a turbine engine. A better understanding and better modeling of these phenomena makes it possible to dimension all of the members in the fuel feed system, and in particular the fuel pump, as well as possible.

According to a proposed characteristic, the test bench includes means suitable for heating or cooling the fluid, such as a heat exchanger for example.

It is thus possible to study the above-mentioned V/L ratios for different temperatures of the fluid. Such means also make it possible to maintain the fluid at a constant temperature throughout the duration of a test, for example.

By way of example, the means suitable for heating or cooling the fluid are situated upstream from the first and second lines. The means may be formed by a heat exchanger suitable for exchanging heat between said fluid and a transfer fluid, e.g. water.

The first line may include a first regulator valve situated downstream from the second pump, with the second line including a second regulator valve situated downstream from the Venturi.

The first and second regulator valves are adjustable, and each makes it possible to generate adjustable back pressure in the corresponding line so as to control the flow rate in each of the lines. These valves make it possible in particular to obtain identical fluid flow rates in both lines.

Preferably, the first line includes a third regulator valve situated upstream from the second pump and downstream from the first measurement means, the second line including a second regulator valve situated upstream from the Venturi and downstream from the second measurement means.

The third and fourth regulator valves are also adjustable, and each of them makes it possible to refine the adjustment of the fluid flow rate in each of the first and second lines. By means of the first, second, third, and fourth regulator valves, two degrees of freedom are provided for adjusting the back pressure in each of the lines.

Furthermore, the first line may include a fifth regulator valve situated upstream from the first air injection means, the second line including a sixth regulator valve situated upstream from the second air injection means.

The fifth and sixth valves are adjustable and form singular head losses.

Furthermore, the first line may include third measurement means suitable for providing information about the proportion of the vapor phase relative to the liquid phase of the fluid, and situated downstream from the second pump, the second pump being a centrifugal pump.

On passing through the second pump, different chemical species have different behaviors. The presence of the third measurement means make it possible, in comparison with the information provided by the first measurement means, to determine the contribution of each chemical species in the vapor phase of the fluid. It is thus made possible, for example, to determine the quantities of air and of vaporized kerosene that are present in the vapor phase of the fluid.

Advantageously, the tank is provided with a vacuum pump. In this way, it is possible to recover the vapor phase generated in each of the first and second lines. The vacuum pump also makes it possible to reduce the pressure in the tank, which can have an influence on the quantity of air that is dissolved in the kerosene, for example.

The proposed bench may also include a third line connecting the tank to the first and second lines, the third line including bend zones and zones at various heights, so as to be representative of a fuel feed pipe of a turbine engine.

Finally, the test bench may include means for measuring the flow rate of fluid and/or means for measuring the pressure of the fluid, and/or means for measuring the temperature of the fluid, in each of the first and second lines.

BRIEF DESCRIPTION OF THE SEVERAL VIEWS OF THE DRAWINGS

The invention can be better understood and other details, characteristics, and advantages of the invention appear on reading the following description made by way of non-limiting example and with reference to the accompanying drawings, in which.

DETAILED DESCRIPTION OF THE INVENTION

Figure 1:
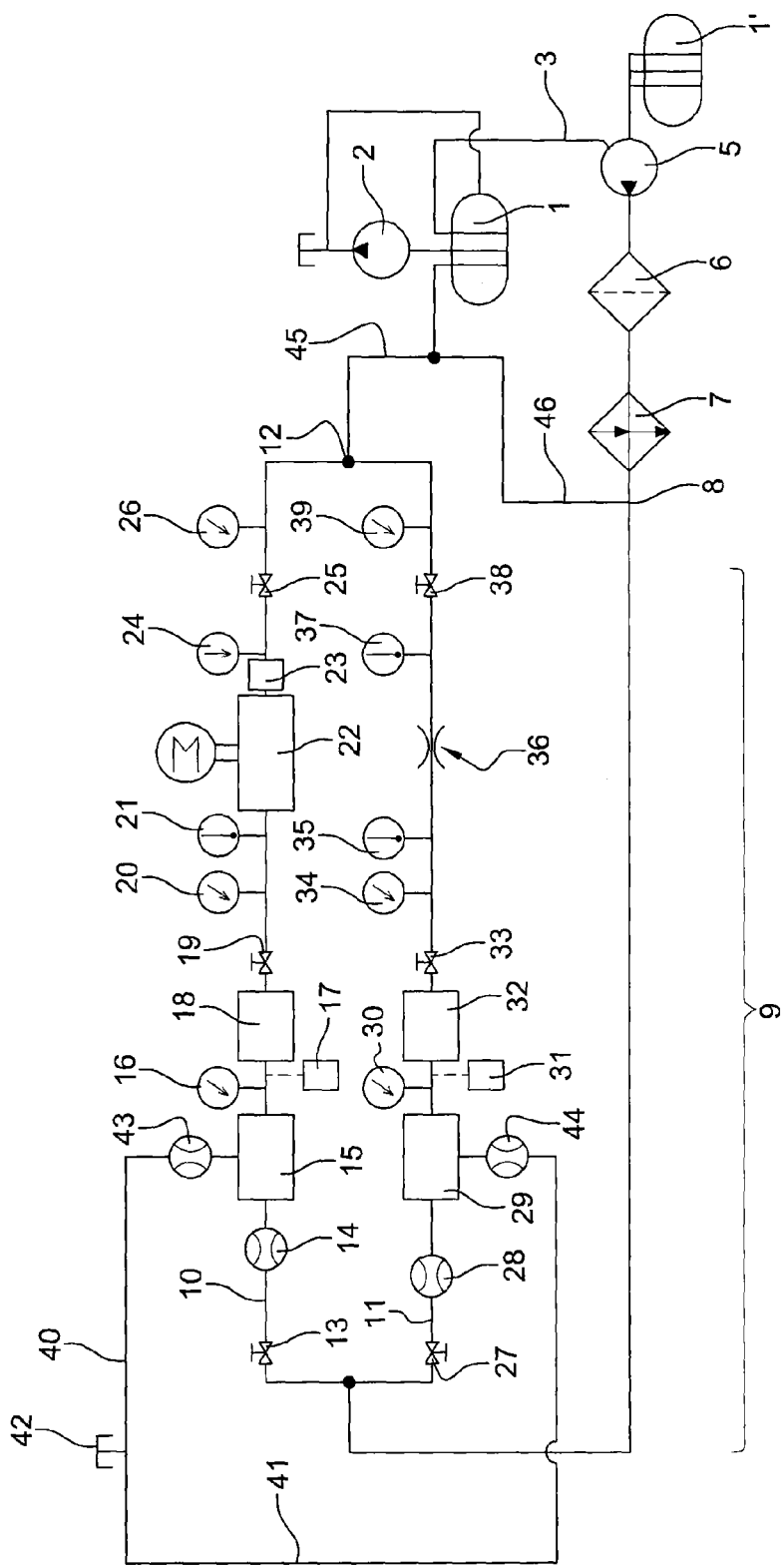
FIG. 1 is a diagram of a test bench in an embodiment of the invention.
Figure 2:
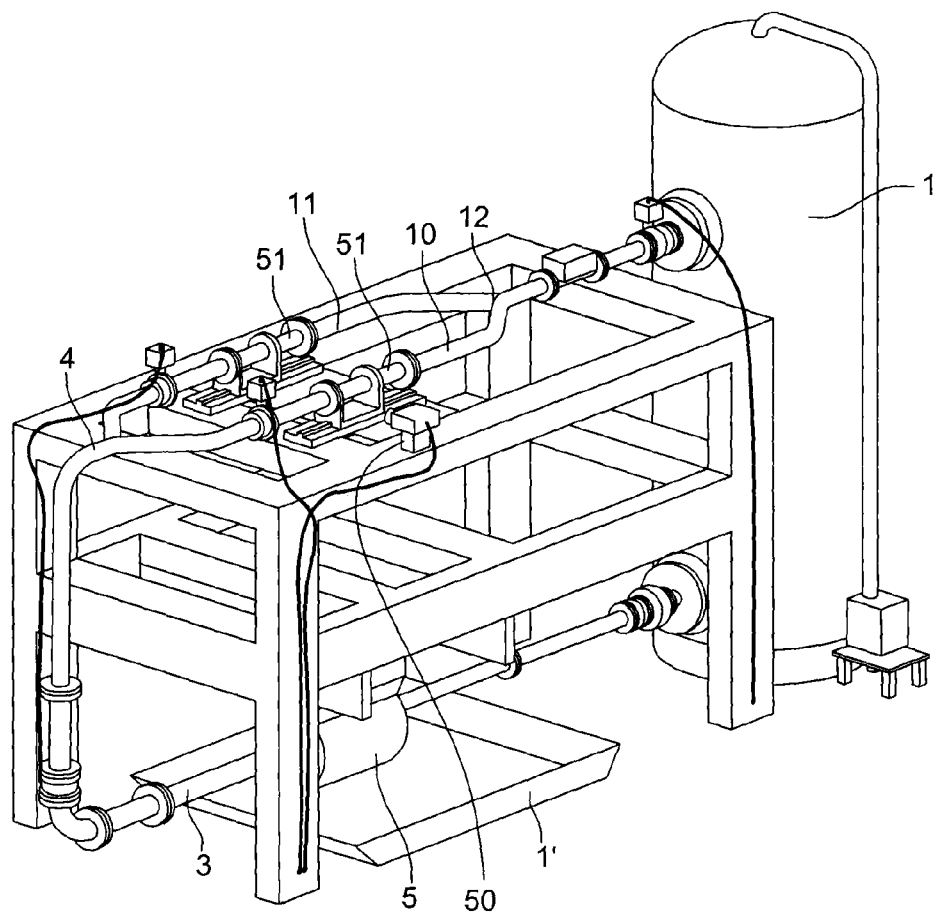
FIG. 2 is a diagrammatic perspective of the FIG. 1 bench.

FIGS. 1 and 2 show a test bench in an embodiment of the invention, said bench being for characterizing a flow of two-phase fluid.

The bench comprises a fluid tank 1 of large capacity, e.g. about 10,000 liters, and containing kerosene, e.g. kerosene of the Jet A1/JP8 type.

The tank 1 has a vacuum pump 2 so as to enable the pressure inside the tank 1 to be adjusted or regulated. The tank is also pressurized with nitrogen.

A line 3 connects an outlet from the tank 1 to a junction 4, said line 3 being provided in succession, from upstream to downstream in the flow direction of the fluid, with: a positive displacement pump 5 suitable for generating a determined flow rate; a filter 6; and a heat exchanger 7 suitable for cooling or heating the fluid. The positive displacement pump 5 is conventionally coupled to a drain tank 6. The heat exchanger 7 is suitable for exchanging heat between the fluid flowing in the line 3, namely kerosene, and a heat transfer fluid such as water, for example.

A junction 8 is situated between the junction 4 and the outlet from the heat exchanger 7.

Although not shown, in the zone 9 situated between the junction 4 and the heat exchanger 7, the line 3 has a succession of bends, e.g. seven 90° bends, constrictions suitable for forming singular head losses, and zones situated at different heights so as to reproduce as accurately as possible the configuration of a fuel feed pipe of an airplane.

Downstream from the junction 4 there extend two parallel lines given respective references 10 and 11, the downstream ends of these lines being united by a junction 12.

The line 10 is provided in succession, from upstream to downstream, with: an expansion valve 13; a flow meter 14; means 15 for injecting a flow of air into the kerosene; a pressure sensor 16; a light sensor 17; a sensor 18 suitable for determining the proportion of vapor phase in the fluid flowing in said line 10; an expansion valve 19; a pressure sensor 20; a temperature sensor 21; a centrifugal pump 22 having a bladed impeller; a sensor 23 suitable for determining the proportion of vapor phase in the fluid flowing in said line 10; a turbine sensor 24; an expansion valve 25; and a pressure sensor 26.

The line 11 is provided in succession, from upstream to downstream, with: an expansion valve 27; a flow meter 28; means 29 for injecting a flow of air into the kerosene; a pressure sensor 30; a light sensor 31; a sensor 32 suitable for determining the proportion of vapor phase in the liquid flowing in said line; an expansion valve 33; a pressure sensor 34; a temperature sensor 35; a Venturi 36; a temperature sensor 37; an expansion valve 38; and a pressure sensor 39.

The lines 10 and 11 thus present the same characteristics (same expansion valves or regulator valves, same line lengths, etc. . . . ) with the exception of the presence of the pump 22 and of the sensor 23 in one of the lines and the presence of the Venturi 36 in the other line. This makes it easier to compare the measurements taken in each of the lines 10 and 11.

Compressed air feed lines 40 and 41 connect a compressed air tank 42 to the injection means 15 and 29 of the first and second lines 10 and 11 via flow meters 43 and 44.

A line 45 connects the junction 12 to an inlet of the tank 1. A short-circuit line 46 connects the junction 12 or the line 45 of the line 3 via the junction 8 situated between the heat exchanger 7 and the junction 4.

Figure 3:
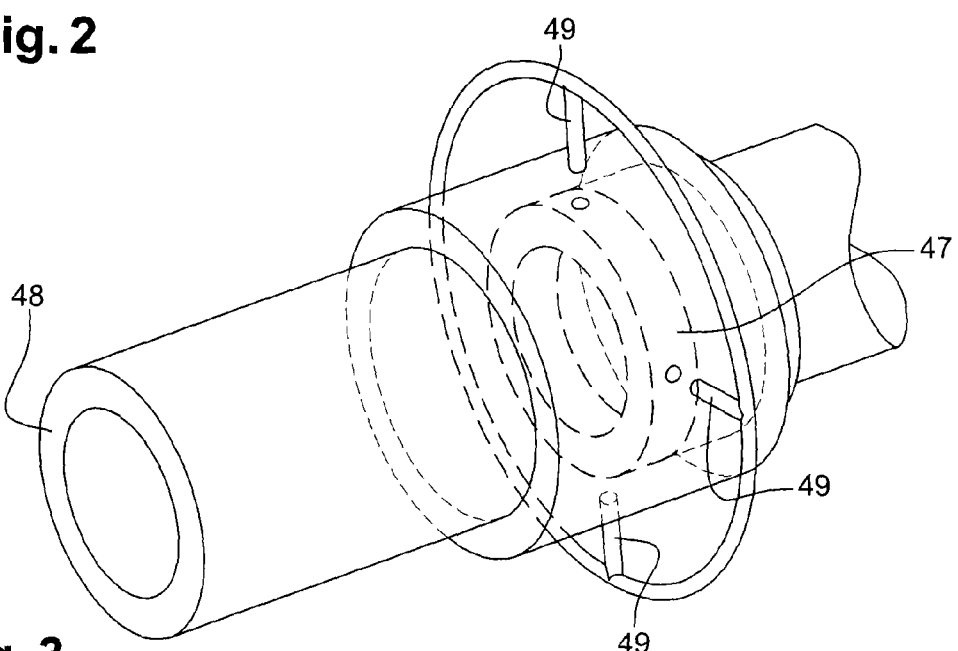
FIG. 3 is a perspective view of a portion of the air injection means.

As can be seen more clearly in FIG. 3, each of the air injection means 15, 29 comprises a respective ring 47 of porous material having an inside diameter that corresponds substantially to the inside diameter of the corresponding pipe 48 of the line 10 or 11. Air under pressure from the lines 40 and 41 is delivered via four tubes 49 into the ring 47, with this air then diffusing into the fluid over the entire periphery of the ring 47 through its pores. The tubes 49 are regularly distributed around the circumference and they are annularly offset from one another at 90°. The size and the quantity of the bubbles as generated in this way depend on the air pressure upstream from the ring 47 and on the characteristic size of the pores of the ring 47. The ring 47 is removable, and may be changed, depending on requirements.

Each light sensor 17, 31 comprises a camera 50 (FIG. 3) capable of acquiring up to 10,000 images per second, depending on the desired resolution. The images are stored in a temporary memory and they be conveyed to a computer for processing. The camera is positioned facing a transparent portion 51 of the line 10, 11. This portion 51 is made by a transparent segment of pipe that is made of a material presenting substantially the same surface state as the remainder of the line 10, 11. By way of example, such pipes are known under the trademark Manuled and sold by Tecalemit Flexibles.

A lighting plate (not shown) having light emitting diodes (LEDs) may be placed behind the pipe so as to illuminate the corresponding zone 51 in uniform manner and thereby facilitate image processing.

Such processing serves to determine the occurrence and the quantity of bubbles or pockets of gas in the fluid.

Each of the measurement means 18, 23, 32 has measurement electrodes that are spaced apart from one another so as to define concentric spaces therebetween subdividing the flow section of the corresponding line 10, 11. An excitation electric signal is applied between the measurement electrodes and serves to measure a value that is representative of the gas content of the fluid passing along the line.

In operation, it is possible to vary or regulate the following parameters:
  the pressure inside the tank 1, by means of the vacuum pump 2;
  the temperature of the fluid flowing through the test bench, by means of the heat exchanger 7;
  the flow rate of the air injected into each line 10, 11 by the injection means 15, 29;
  the speed of rotation of the pump 22;
  the fluid flow rate delivered by the pump 5;
  the head losses or back pressures generated by each of the expansion valves 13, 19, 25, 27, 33, 38; and
  the flow rate of the fluid diverted via the bypass line 46, possibly via an adjustable valve that is not shown.

All of these parameters have an influence on the proportion of gas in the fluid at various locations of the test bench. The measurements taken with the help of the various sensors thus serve to understand the phenomena involved and, consequently, to adapt mathematical models so that they represent reality as accurately as possible. The challenge is in particular to be able to improve the dimensioning of the fuel pump for a turbine engine in order to optimize both its size and its weight.

Such a test bench makes it possible to study in depth the interface between the kerosene feed (tank 1, pump 5, special shape of the zone 9 of the line 3) and the turbojet (including in particular the fuel pump that is simulated in part in the bench by the pump 22). The ratios of vapor phase proportion over liquid phase proportion (V/L ratio) as measured with the help of the sensors 18, 23, 32 serve to characterize the operation of this interface in the presence of gas. The bench of the invention is thus capable of generating any type of V/L ratio in a pipe presenting shapes similar to or identical to the stages of a pipe forming part of an airplane. The bench also makes it possible to distinguish between the mutual influences on the above-mentioned phenomena that are due to the turbine engine proper and that are due to the remainder of the airplane.

The invention claimed is:

1. A test bench for characterizing a flow of a two-phase fluid, the bench comprising:
   a fluid tank; and
   a first pump suitable for taking fluid from the tank and for feeding first and second lines that are connected in parallel;
   the first line being provided in succession, from upstream to downstream in a fluid flow direction, with: a first air injector which injects air into the fluid; a first sensor which provides information about a proportion of a vapor phase relative to a liquid phase of the fluid; and a second pump suitable for simulating a turbine engine fuel pump;
   the second line being provided in succession, from upstream to downstream in the flow direction of the fluid, with: a second air injector which injects air into the fluid, a second sensor which provides information about the proportion of the vapor phase relative to the liquid phase of the fluid; and a suction-generator member.

2. The test bench according to claim 1, further comprising a heat exchanger.

3. The test bench according to claim 2, wherein the heat exchanger is situated upstream from the first and second lines.

4. The test bench according to claim 1, wherein the first line includes a first regulator valve situated downstream from the second pump, with the second line including a second regulator valve situated downstream from the suction-generator member.

5. The test bench according to claim 1, wherein the first line includes a third regulator valve situated upstream from the second pump and downstream from the first sensor, and the second line includes a second regulator valve situated upstream from the suction-generator member and downstream from the second sensor.

6. The test bench according to claim 1, wherein the first line includes a fifth regulator valve situated upstream from the first air injector, and the second line includes a sixth regulator valve situated upstream from the second air injector.

7. The test bench according to claim 1, wherein the first line includes a third sensor which provides information about the proportion of the vapor phase relative to the liquid phase of the fluid, and situated downstream from the second pump, the second pump being a centrifugal pump.

8. The test bench according to claim 1, wherein the tank is provided with a vacuum pump.

9. The test bench according to claim 1, further comprising a third line connecting the tank to the first and second lines, the third line including bend zones and zones at various heights.

10. The test bench according to claim 1, further comprising at least one of a sensor which measures a flow rate of fluid, a sensor which measures a pressure of the fluid, and a sensor which measures a temperature of the fluid, in each of the first and second lines.

11. The test bench according to claim 1, wherein the suction-generator member is a Venturi.

* * * * *